United States Patent [19]
Ikegami et al.

[11] Patent Number: 6,050,956
[45] Date of Patent: Apr. 18, 2000

[54] HEMOLYZING TUBE AND A METHOD OF PREPARING A HEMOLYSIS BLOOD SAMPLE WITHIN TUBE

[75] Inventors: Takashi Ikegami, Osaka; Shinichiro Harada, Osaka-fu; Joachim Oehler, Tokyo, all of Japan

[73] Assignee: Nissho Corporation, Osaka, Japan

[21] Appl. No.: 09/102,623

[22] Filed: Jun. 23, 1998

[51] Int. Cl.⁷ ...................................................... A61B 5/00
[52] U.S. Cl. ............................................................ 600/573
[58] Field of Search .................................... 600/573, 576, 600/577, 579, 583

[56] References Cited

U.S. PATENT DOCUMENTS

| | | | |
|---|---|---|---|
| 5,181,523 | 1/1993 | Wendelborn | 600/577 |
| 5,360,012 | 11/1994 | Ebara et al. | 128/764 |
| 5,743,861 | 4/1998 | Columbus et al. | 600/577 |
| 5,763,033 | 6/1998 | Tropsha et al. | 428/36.7 |
| 5,906,744 | 5/1999 | Carroll et al. | 210/516 |

*Primary Examiner*—Max Hindenburg
*Attorney, Agent, or Firm*—Kubovcik & Kubovcik

[57] ABSTRACT

A hemolyzing tube (A) having its interior (10) evacuated and containing a standard amount of a blood dissolving liquid (3) has a tubular body (2) whose closed bottom faces a top mouth closed with a stopper (1) capable of being pierced. The tube is usable with a cylindrical casing (C) having a double-ended needle (8) and also with an evacuated blood collection tube (B) that is for temporary accommodation in the casing. In the method of preparing a hemolysis blood sample, a small amount of blood sucked through the needle will enter the collection tube (B), and a residual amount of blood remaining in the needle will then be drawn into the hemolyzing tube (A) to produce in it a test sample subject to clinical examination of the blood.

10 Claims, 5 Drawing Sheets

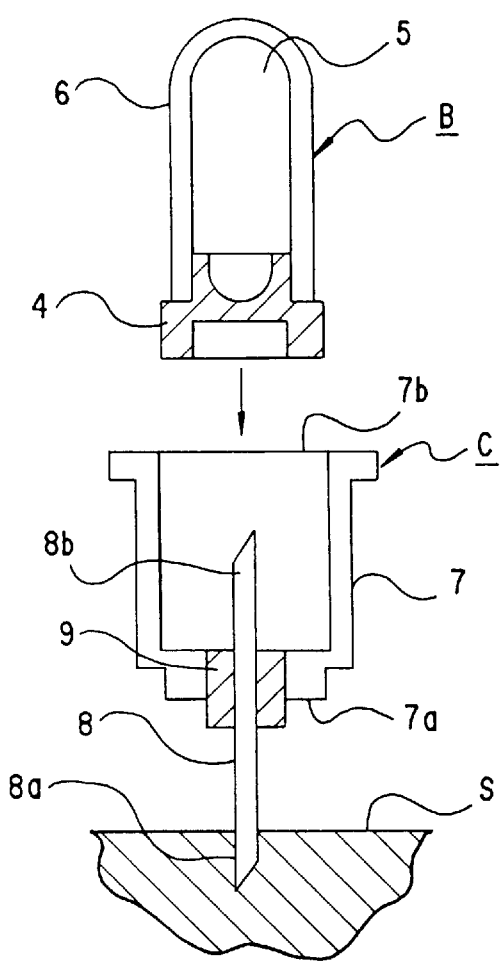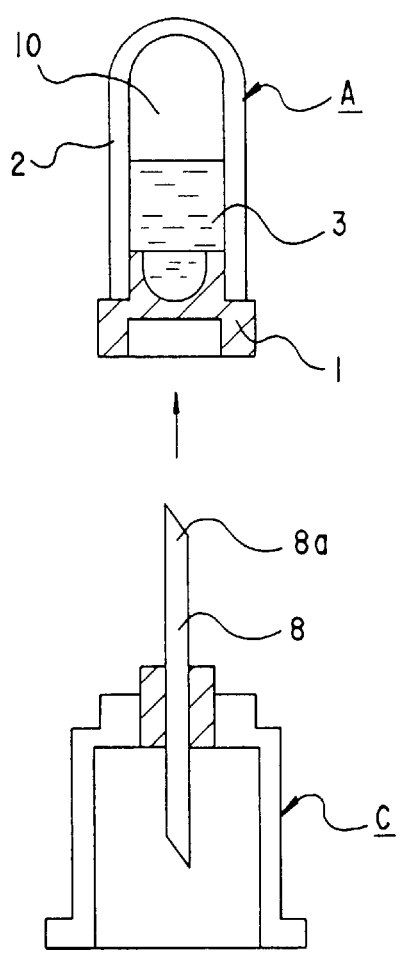

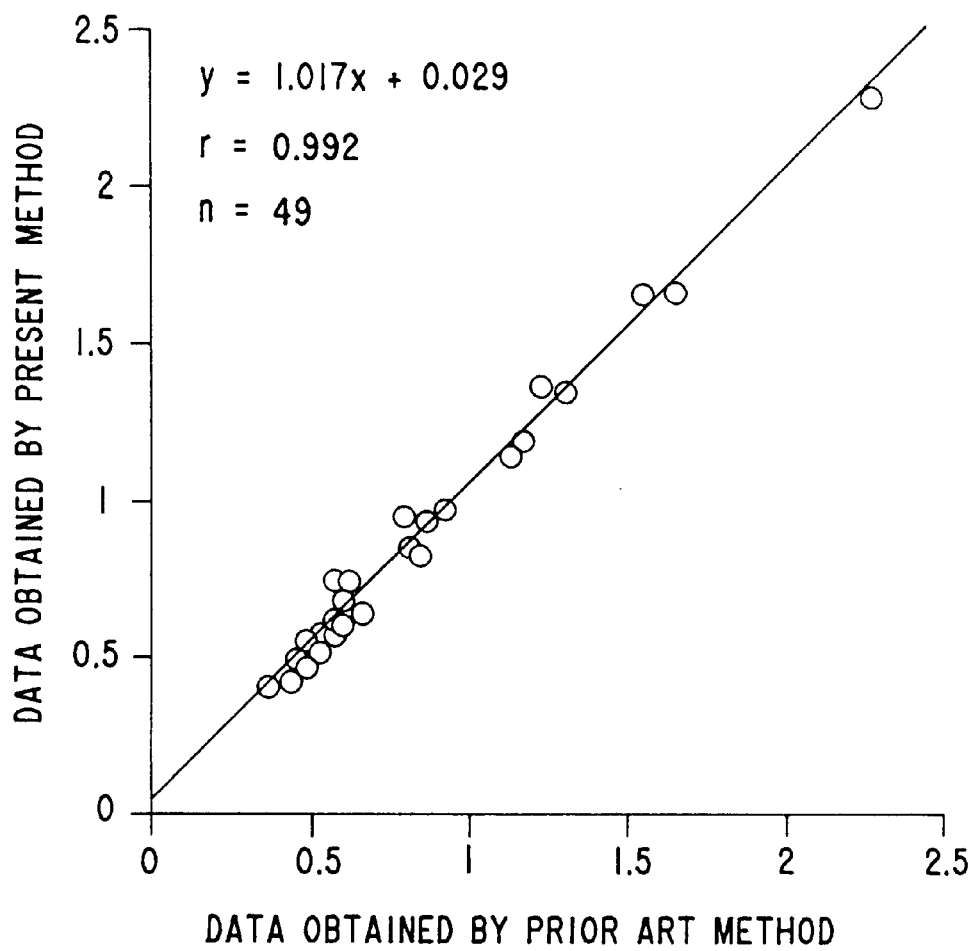

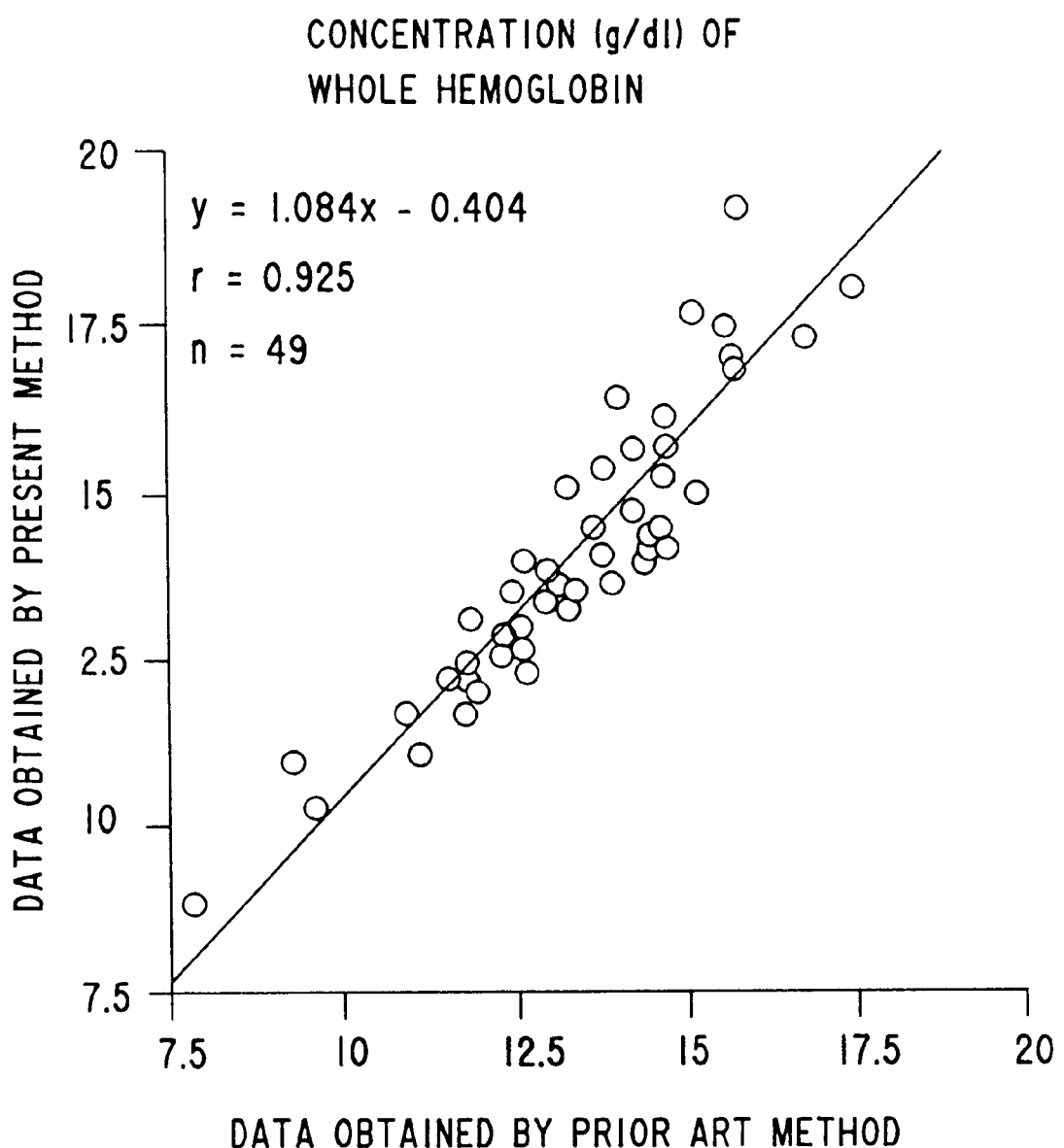

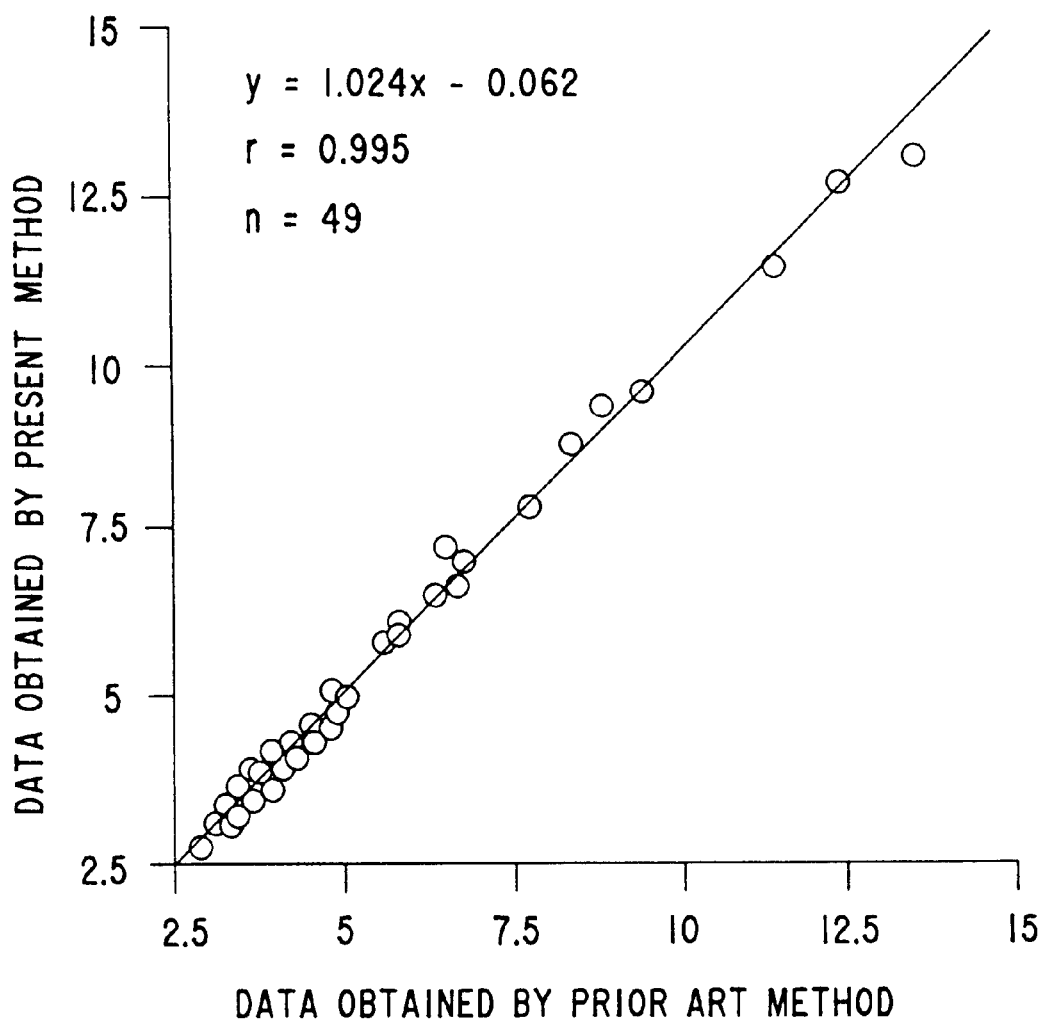

HEMOLYZING TUBE AND A METHOD OF PREPARING A HEMOLYSIS BLOOD SAMPLE WITHIN TUBE

BACKGROUND OF THE INVENTION

The present invention relates to a hemolyzing tube containing a blood dissolving liquid and relates also to a method of preparing a hemolysis blood sample within the hemolyzing tube, wherein a very small amount of blood is diluted in the liquid for the purpose of clinical examinations.

In general, clinical blood examinations including an analytical measurement of hemoglobin are important in diagnostic determinations of diabetes, kidney or renal troubles and the like diseases. In the case of hemoglobin measurement, syringes, evacuated blood-collecting tubes or the like are used at first to take blood samples that will then be transferred into certain preparatory test tubes. Subsequently, a small prescribed amount of the blood sample is sucked into a micropipet, a spoid or the like itemizer, prior to injection of the sample into a standard test tube. A required amount of a blood dissolving liquid will have been provided in the standard test tube so that a regular sample of a regulated concentration is prepared in this tube. The regular sample will then be subjected to so-called high speed liquid chromatography (viz., HPLC method) to determine the quantity and/or quality of hemoglobin. In another case, a required small amount of the collected blood sample will be diluted with water so as to convert hemoglobin into oxyhemoglobin. Absorptiometric analysis will be conducted on such a diluted sample in order to detect absorption at a wavelength of 540 nm also for the same purposes as above.

General prior art methods of preparing dissolved blood samples are, however, disadvantageous from various points of view. Each amount of raw blood sample is exposed to ambient air during preparation, thereby causing not only pollution of said sample with air but also possibly scattering it to adjacent objects. In the case of using the evacuated blood sampling tubes, it has been necessary for medical service persons to remove a rubber stopper from each sampling tube at first, before using a micropipet to suck a small required amount of blood. Such an operation has been intricate and required much labor particularly to intently watch fine scales on the micropipet. If spoids are additionally used, then variable finger pressure will vary amounts of squeezed blood drops, thus bringing about a noticeable inaccuracy in results of the following hematoscopy test.

SUMMARY OF THE INVENTION

The present invention was made in view of the various drawbacks inherent in the prior art systems summarized above. An object of the invention is, therefore, to provide a hemolyzing tube (viz., a blood dissolving tube) designed such that a small amount of blood being taken out of a human body is protected from contacting ambient air during transfer of said blood into the tube. The blood sample thus received in said tube will be diluted therein to be subjected to clinical examinations. Another object of the present invention is to provide a novel method of simply and easily preparing a hemolysis blood sample (viz., a dissolved blood sample), in such a manner that during the whole process the blood is never exposed to ambient air.

The present inventors became aware of a possibility of utilizing a small residual amount of blood remaining in a double-ended medical needle. In accordance with the prior art systems each employing an evacuated blood collection tube in combination with an external cylindrical casing, the double-ended needles had been removed from the cylinder and discarded after every use at the initial stage of collecting a blood sample. Researches have been made by the present inventors on how to make use of such a remaining amount of blood staying in each double-ended needle. They have become cognizant of a fact that the actual amount of remaining blood almost constantly depends on the respective specifications of the double-ended needles to such a degree that exact and satisfactory samples of dissolved blood could be prepared using, the remaining blood.

A hemolyzing tube provided herein and remaining evacuated, i.e., the inside of the tube being under reduced pressure, contains a standard amount of blood dissolving liquid and comprises a closed bottom and a top mouth closed with a stopper capable of being pierced.

A method proposed herein to prepare a hemolysis blood sample in accordance with the present invention comprises the steps of making available a hemolyzing tube remaining evacuated, containing a blood dissolving liquid and having a top mouth closed with a stopper as summarized above, and making available a cylindrical casing for use with and for accommodation of an evacuated blood collection tube having a closed bottom and a top mouth closed with a stopper, wherein a double-ended needle is disposed to penetrate a closed end of the cylindrical casing. The method further comprises the successive steps of causing an outer end of the double-ended needle to prick the wall of a blood vessel under a human skin, placing the blood collection tube in the cylindrical casing, causing an inner end of the double-ended needle to pierce the stopper of the blood collection tube so as to let an amount of blood flow into the collection tube, subsequently removing the cylindrical casing from the human skin and removing the collection tube from the cylindrical casing, and finally causing the outer end of the double-ended needle to pierce the stopper closing the top mouth of the hemolyzing tube so that the amount of blood remaining in the double-ended needle transfers into the hemolyzing tube and consequently becomes dissolved in the blood dissolving liquid within said hemolyzing tube.

BRIEF DESCRIPTION OF THE DRAWINGS

In the drawings showing some embodiments of the present invention,

FIG. 2a is a cross section of an assembly of members operated at one step of a method proposed herein;

FIG. 2b is a similar cross section of another assembly at a further step following the one step;

FIG. 3 is a graph showing the concentration of hemoglobin fraction A1c measured by the present method in comparison with that measured by the prior art method;

FIG. 4 is a graph corresponding to FIG. 3 but showing data observed as to whole hemoglobin; and FIG. 5 is a graph showing the ratio of the concentration of hemoglobin fraction to the concentration of whole hemoglobin, the ratio being calculated on the basis of data shown in FIGS. 3 and 4.

DESCRIPTION OF THE PREFERRED EMBODIMENTS

Figure 1:
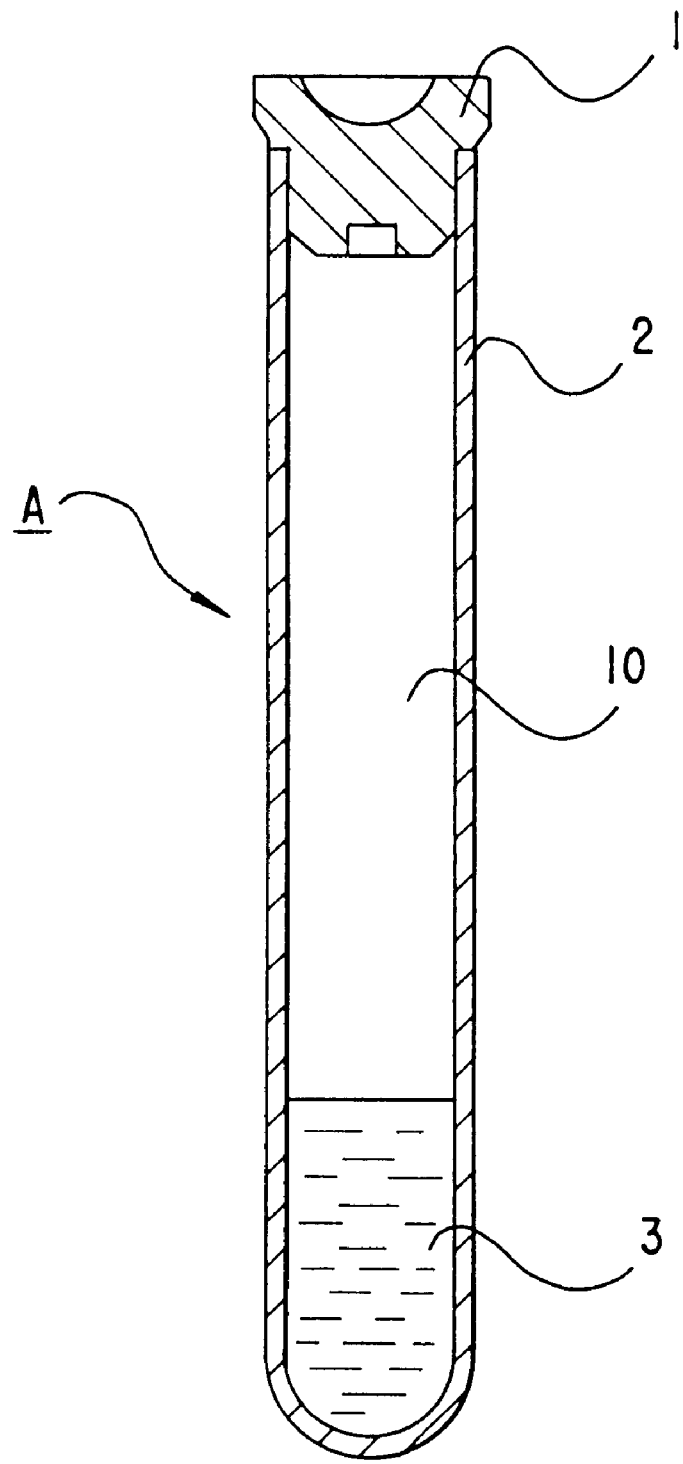
FIG. 1 is a longitudinal cross section of a hemolyzing tube in an embodiment of the invention.

Now some embodiments of the present invention will be described referring to the drawings.

As seen in FIGS. 1 and 2b, a hemolyzing tube "A" provided herein comprises a tubular body 2 made of an appropriate plastic or glass. The tubular body 2 has a closed bottom and a top mouth that is closed tightly with a stopper 1. The tube "A" is designed to hold therein a proper amount of a blood dissolving liquid 3 and remains evacuated to allow suction of a proper amount of sample blood. The stopper 1 is made of a material capable of being pierced with an injection needle or the like. In detail, the material forming the stopper 1 may be a high quality rubber such as a butyl rubber or a styrene-butadiene rubber. The rubbers of this grade are not gas-permeable but will show a sufficient self-sealing property even after being pierced with the needle.

In a case wherein the tubular body 2 is made of a plastic, its inner surface may be coated with an appropriate water-repellent agent to inhibit the collected blood sample from sticking to said surface of the tubular body. Preferable examples of the plastic forming the tubular body 2 are polyester, polyolefin, polystyrene, polymethyl methacrylate, polycarbonate and the like. Examples of the water-repellent agent include silicone, fluoride resin, polyethylene glycol, paraffin, wax and the like. In another case wherein the tubular body 2 is made of an appropriate glass that is hydrophilic, a layer of water adsorbed on the inner surface will appear naturally when used. Therefore, the water-repellent agents can be dispensed with, but this does not exclude the possibility of employing the same if necessary from any point of view.

The blood dissolving liquid 3 held in the tubular body 2 may be any one selected from the group consisting of: water, a phosphate buffer solution containing tetradecyl-trimethylammonium bromide, a carbonate buffer solution containing alkylphenoxy-polyethoxy ethanol, an ammonium chloride solution, an appropriate solution containing a surfactant and the like solutions. Any appropriate reagent for analyzing blood components such as hemoglobin may be contained in such a blood dissolving liquid 3.

Analytical measurement of hemoglobin may be of any type such as those for determining the concentration of hemoglobin fraction A1c (or whole hemoglobin to determine the latter), and those for determining glycohemoglobin, all important in the diagnosis of diabetes.

Usually, a noticeable amount of surfactant is contained in each buffer solution mentioned above. Accordingly, there is an undesirable possibility that many bubbles or foam are produced during the blood dissolving operation. In such an event, the succeeding step of analyzing the dissolved blood sample may render erroneous the results of hemoglobin measurement. Therefore, medical service persons have to carefully conduct the hemolysis operation not to produce bubbles. The interior 10 of the hemolyzing tube "A" automatically remains evacuated to almost permanently show an absolute air pressure of 60–570 mm Hg.

The method in which the hemolyzing tube "A" as discussed above is used to prepare a human hemolysis blood sample will now be described referring to FIGS. 2a and 2b. FIG. 2a shows the step of collecting a blood sample from a human body, wherein an evacuated blood collection tube "B" is used together with a cylindrical casing "C". This casing "C" comprises a cylinder 7 whose proximal end 7b is open, with its distal end 7a having integral therewith a bottom block 9. A needle double-ended at 8a and 8b penetrates the bottom block 9. One of the ends 8a of the needle 8 protrudes forwards to be able to prick a skin "S" and a blood vessel thereunder, with the other end 8b being uncovered. However, the latter end 8b may be covered with a rubber sheath, if so desired. On the other hand, the blood collection tube "B" comprises a tubular body 6 having a closed 'top' (in the drawings). A bottom mouth of this tube "B" is closed with a rubber stopper 4 so that its interior 5 remains evacuated.

In order to take a blood sample, the blood collection tube "B" is inserted in the cylindrical casing "C", as shown in FIG. 2a. At that time, one end closed with the rubber stopper 4 has to lead the tube "B", until it reaches the bottom block 9 of casing "C". As a result, the proximal end 8b of the double-ended needle 8 will penetrate the rubber stopper 4 to thereby enter the interior 5 of the tube "B". If a rubber sheath is incorporated to cover the proximal end 8b, the latter will also penetrate the former, while folding same several times on the bottom block 9. After or before (preferably after) such a preliminary operation as just described, the distal end 8a of the needle 8 will be forced to prick human skin "S" whereby the interior 5 automatically sucks a small amount of his or her venous blood. This amount of sucked blood depends on the extent to which said interior 5 has been kept evacuated. Upon completion of blood sampling, the tube "B" will be disconnected from the casing "C", after or before (preferably after) taking both "B" and "C" as a whole away from the skin "S" so as to be ready for the succeeding steps.

Next, as shown in FIG. 2b, the distal end 8a of the needle held in place by the cylindrical casing "C" will be pressed against the stopper 1 of the hemolyzing tube "A" so that said end 8a penetrates this stopper 1 and enters this tube's interior 10. This interior 10 having been kept evacuated will thus automatically suck a blood sample residue which has stayed within the needle 8, and said residue will dissolve into the blood dissolving liquid 3. The hemolyzing tube "A" shown in FIG. 2b assumes a posture having its stopper 1 directed downwards, with the distal end 8a of the needle 8 jutting upwards being thereby pushed upwards. It is however a matter of course that they may be turned upside down as a whole so as to push the tube "A" upwards towards the needle.

The quantity of blood sample taken into the interior 10 of the hemolytic tube "A" will almost absolutely depend on the inner diameter and length of the double-ended needle 8. For example, about 13 microliter of blood will remain in each of needles of the nominal type '21G', whereas about 10 microliter remains in each needle of type '22G' when used in the described manner. Therefore, an optimal amount of the blood dissolving liquid 3 held in each tube "A" can readily and previously be determined to ensure a desired degree of dilution.

EXAMPLE 1

Double-ended needles '22G' (made by Nipro Corp., a Japanese company) were respectively attached to cylindrical casings (Nipro's 'holders' for blood collecting needles), and evacuated blood collection tubes (of Nipro's type PS0505) were inserted in the respective casings. On the other hand, hemolyzing tubes (made of a glass and each having a volume of 3 ml) were prepared, and 1 ml of blood dissolving liquid hemolyzing reagent (Tina quant a HbA1c, Tina quant a HbA1cII, a reagent made by BOEHRINGER MANNHEIM GmbH, a German company) was received in each hemolyzing tube. By piercing tight rubber stoppers closing the hemolytic tubes with the needles, a small amount of blood staying in each needle transferred into each of these tubes so as to be dissolved therein at a dilution ratio of 101. Forty-nine blood samples prepared in this manner were then subjected to immunonephelometry to measure concentration (g/dl) of hemoglobin fraction A1c and gave the results shown in FIG. 3. Similarly, another group of forty-nine blood samples were tested by chromometry at a wavelength of 570 nm to determine concentration (g/dl) of whole hemoglobin, giving the results shown in FIG. 4. The immunonephelometry for fraction A1c is based on an antigen-antibody reaction, such that antigen molecules contained in the reagent and acting against hemoglobin A1c will be caught thereby. The remainder of the antigen molecules form bonds between the same and 'poly-haptene' to thereby produce complexes that enable turbidimetery at a wavelength of 340 nm and using a correlation line.

REFERENCE 1

Cylindrical casings and blood collection tubes, all being the same as those in EXAMPLE 1, were used to collect human blood samples into said tubes. Then 0.01 ml of each sample was taken using a micropipet so as to be dropped into each of test tubes in which 1 ml of hemolyzing reagent (see above) was contained. Ratio of dilution was thus 101, also in this case, and forty-nine samples 15 were tested to determine concentration (g/dl) of hemoglobin fraction Aic and concentration (g/dl) of whole hemoglobin. The results obtained in this manner are shown in FIGS. 3 and 4, in comparison with the data obtained in EXAMPLE 1.

As will be seen clearly in FIGS. 3 and 4, the data obtained in EXAMPLE 1 (i.e., the method of the invention) coincided well with those obtained in REFERENCE 1 (i.e., the prior art method). Straight lines drawn in FIGS. 3 and 4 indicate that a substantially proportional correlation is present between the two methods as to both the concentrations of whole hemoglobin and its fraction A1c. It is supposed that protection of the fresh blood samples from contamination with ambient air plays an important role to render feasible the hemolyzing tube of the present invention, and consequently to provide a reliable method that can substitute for the prior art method.

FIG. 5 shows ratio (%) of hemoglobin fraction A1c to whole hemoglobin, wherein concentration of the former is divided by concentration of the latter and multiplied by 100. As seen in FIG. 5, a linear (viz., proportional) correlation was also confirmed between the method of the present invention (EXAMPLE 1) and the prior art method (REFERENCE 1).

In summary, the hemolytic tube which the present invention offers is advantageous in that each blood sample taken out of a human body is not exposed to ambient air until and after it will have been diluted in the dissolving liquid in said tube. The blood samples are thus not only protected from being contaminated with air but also inhibited from scattering to soil adjacent objects.

Further, the method proposed herein does not require any intricate operations and has a characteristic feature that each double-ended needle naturally gives a constant amount of blood sample, depending on its dimensional specification. Thanks to this feature, each of the blood samples can transfer into an evacuated blood collection tube and then directly into a hemolyzing tube where it is diluted to give a final hemolysis sample subject to various clinical examinations. Protection of blood samples from ambient air and protection of adjacent objects from the blood samples are afforded also by this method. In addition, it is now possible to make use of the small amount of blood remaining in each needle and heretofore having been discarded, for the purpose of preparing a blood sample for measuring the concentration of hemoglobin or the like.

What we claim is:

1. A hemolyzing tube comprising a tubular body, the tubular body having a closed bottom and a top mouth, wherein said top mouth is closed with a stopper capable of being pierced and an inside of said tubular body is under reduced pressure; and a solution for hemolyzing blood samples contained in said tubular body.

2. A hemolyzing tube as defined in claim 1, wherein the blood dissolving liquid contains at least one reagent for use in examination of blood fractions.

3. A hemolyzing tube as defined in claim 2, wherein said at least one reagent is provided for measurement of concentration of hemoglobin and of fractions thereof.

4. A hemolyzing tube as defined in claim 1, wherein the tubular body is formed of a plastic and has an inner wall surface coated with a water-repellent material which repels blood.

5. A hemolyzing tube as defined in claim 2, wherein the tubular body is formed of a plastic and has an inner wall surface coated with a water-repellent material which repeles blood.

6. A hemolyzing tube as defined in claim 3, wherein the tubular body is formed of a plastic and has an inner wall surface coated with a water-repellent material which repels blood.

7. A hemolyzing tube as defined in claim 1, wherein the tubular body is formed of a glass.

8. A hemolyzing tube as defined in claim 2, wherein the tubular body is formed of a glass.

9. A hemolyzing tube as defined in claim 3, wherein the tubular body is formed of a glass.

10. A method of preparing a hemolysis blood sample, comprising the steps of:

preparing a hemolyzing tube comprising a tubular body, the tubular body having a closed bottom and a top mouth, wherein said top mouth is closed with a stopper capable of being pierced and an inside of said tubular body is under reduced pressure; and a blood dissolving liquid contained in said tubular body;

preparing a cylindrical casing having a closed end and an open end for use with and for accommodation of an evacuated blood collection tube having a closed bottom and a top mouth closed with a second stopper, wherein a double-ended needle having inner and outer ends is disposed in and penetrates said closed end of the cylindrical casing;

thereafter pricking a wall of a blood vessel under a human skin with said outer end of the double-ended needle and placing the blood collection tube in the cylindrical casing;

piercing said second stopper with said inner end of the double-ended needle so as to let an amount of blood flow into the collection tube;

subsequently removing the cylindrical casing from the human skin and taking the collection tube out of the cylindrical casing; and finally causing said outer end of the double-ended needle to pierce the first stopper closing the top mouth of the hemolyzing tube so that an amount of blood remaining in the double-ended needle transfers into the hemolyzing tube and consequently becomes dissolved in the blood dissolving liquid within said hemolyzing tube.

\* \* \* \* \*